US00PP17690P2

(12) United States Plant Patent
Hofmann

(10) Patent No.: US PP17,690 P2
(45) Date of Patent: May 1, 2007

(54) **NEW GUINEA *IMPATIENS* PLANT NAMED 'FISNICS PURDEEP'**

(50) Latin Name: *Impatiens hawkeri*
Varietal Denomination: Fisnics Purdeep

(75) Inventor: Birgit Christa Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/330,444

(22) Filed: Jan. 12, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Anne Marie Grunberg
*Assistant Examiner*—Georgia Helmer
(74) *Attorney, Agent, or Firm*—Jondle & Associates P.C.

(57) ABSTRACT

A new New Guinea *Impatiens* plant particularly distinguished by large, round, flat to slightly cup-shaped deep purple flowers, early flowering, deep green foliage with large leaves, and a medium size plant habit that is round and bushy, is disclosed.

1 Drawing Sheet

Genus and species: *Impatiens hawkeri* W. Bull.
Variety denomination: 'Fisnics Purdeep'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name 'Fisnics Purdeep'. The new cultivar originated from a hybridization made in the year 2002 in Hillscheid, Germany. The female parent was the proprietary New Guinea *Impatiens* plant 'K02-1080-1' (unpatented), while the male parent was the proprietary New Guinea *Impatiens* plant 'K02-9604-2' (unpatented). The seeds produced by the hybridization were sown in Portugal in the late Fall of 2002. A single plant selection was chosen for further evaluation and for asexual propagation in April 2003 in Moncarapacho, near Faro, Portugal.

The new cultivar was created in 2002 in Hillscheid, Germany and has been asexually reproduced repeatedly by vegetative cuttings and tissue culture in Moncarapacho, Portugal and Hillscheid, Germany over a two-year period. 'Fisnics Purdeep' has not been observed under all possible environmental conditions. The present invention has been found to retain its distinctive characteristics through successive asexual propagations.

Plant Breeder's Rights for this cultivar were applied for in Switzerland on Mar. 30, 2005 and in Canada on Apr. 20, 2005.

SUMMARY OF THE INVENTION

The following are the most outstanding and distinguishing characteristics of this new cultivar when grown under normal horticultural practices in Hillscheid, Germany and Langley, British Columbia, Canada.

1. Uniform, deep purple flower color;
2. Large, round, flat to slightly cup-shaped flowers;
3. Deep green foliage with large leaves;

4. A medium size, round and bushy plant habit; and
5. An early flowering response.

DESCRIPTION OF PHOTOGRAPH

This new New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 13- to 14-weeks old, grown in a greenhouse in Hillscheid, Germany, in late Spring.

DESCRIPTION OF THE NEW CULTIVAR

The following detailed descriptions set forth the distinctive characteristics of 'Fisnics Purdeep'. The data which define these characteristics were collected from asexual reproductions carried out in Hillscheid, Germany. The plant history was taken on 11- to 12-week old plants which were planted as rooted cuttings in 12-cm pots in late February 2005, and then grown in a greenhouse at a minimum temperature of 16° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens hawkeri* W. Bull.
*Common name.*—New Guinea *Impatiens.*

Parentage:
*Female parent.*—'K02-1080-1' a proprietary red-purple flowered New Guinea *Impatiens* plant (unpatented).
*Male parent.*—'K02-9604-2' a proprietary deep cherry-red flowered New Guinea *Impatiens* plant (unpatented).

Growth:

*Growth and branching habit.*—Medium size, round, bushy, and well-branched; the growth is indeterminate, though weak after the beginning of flowering.

*Height.*—14.0 cm.

*Width.*—23.0 cm.

*Propagation.*—Terminal tips for cuttings.

*Time to produce a finished flowering plant.*—9 weeks for a 12-cm pot.

*Time to initiate and develop roots.*—18 days at 22° C.

Branches:

*Average number.*—6.

*Length of branches.*—9 cm to 11 cm.

*Internode length.*—2.5 cm to 3.5 cm.

*Diameter of branches.*—0.5 cm to 0.7 cm.

*Stem color.*—RHS 185A (dark purple).

Leaves:

*Arrangement.*—Primarily in whorls.

*Size.*—Length: 12.3 cm. Width: 4.4 cm.

*Shape.*—Elliptic.

*Margin.*—Slightly serrate, ciliated.

*Apex.*—Acuminate.

*Base.*—Acute.

*Color* (*mature leaves*).—Upper surface: Close to RHS 139A or between RHS 137A and RHS 139A (medium-green). Lower surface: RHS 138B (light-green).

*Color* (*immature leaves*).—Upper surface: Between RHS 137D and RHS 143A. Lower surface: RHS 138B (light-green).

*Texture.*—Surface is lightly glossy, glabrous, smooth or faintly rippled.

*Venation color.*—Upper surface: RHS 53D (pink). Lower surface: RHS 60A.

*Variegation.*—None.

*Petioles.*—Length: 0.5 cm to 1.5 cm. Diameter: 0.3 cm to 0.4 cm. Color: Upper surface: RHS 53A or RHS 53B. Lower surface: RHS 60A. Texture: Glabrous.

Flower buds:

*Shape.*—Ovoid.

*Size.*—Length: 2.6 cm. Width: 1.5 cm.

*Color.*—More bluish than RHS N66A.

Inflorescence:

*Blooming habit.*—9 weeks after planting of rooted cuttings.

*Inflorescence type.*—Flowers appear solitary in the leaf axils of the upper nodes of the stems.

*Number of flowers per node.*—6 to 8, in various stages of development.

*Flowering season.*—Mainly from March to October, depending on light intensity.

*Lastingness of individual blooms.*—Up to 14 days (in a greenhouse in the Spring at 18° C.).

*Fragrance.*—None.

*Peduncle.*—Color: RHS 185B (brownish-red). Size: Length: 5.0 cm. Diameter: 0.1 cm. Texture: Glabrous, flexible.

Flowers:

*Form of corolla.*—Single-type, 5 petals.

*Shape of corolla.*—Nearly round, with the petals overlapping, almost flat to weakly cup-shaped.

*Corolla size.*—Length: 8.4 cm. Width: 7.7 cm. Depth: 1.0 cm to 1.5 cm.

Petals:

*Shape.*—Cordate, weakly lobed.

*Apex.*—Emarginate, banner petal most often without an incision.

*Base.*—Attenuate.

*Margin.*—Entire.

*Petal size.*—Top: Length: 4.1 cm. Width: 6.8 cm. Lateral: Length: 4.2 cm. Width: 4.9 cm. Lower: Length: 4.2 cm. Width: 5.3 cm.

*Color.*—General color description: Intense purple, uniform. Upper surface: RHS N66A or somewhat deeper, no markings. Lower surface: Between RHS N66A and RHS N74A. Eye Zone: No eye.

*Petal texture.*—Smooth, velvety.

*Aspect.*—Flat.

Spur:

*Shape.*—Downwardly curved.

*Color.*—RHS 53B (reddish).

*Size.*—Length: 6.0 cm to 6.5 cm. Diameter: 0.3 cm (at the flower end).

Reproductive organs:

*Stamens.*—Number: 5 fused. Stamen color (upper surface color): RHS 46B (red). Anthers: Fused, hooded. Pollen color: RHS 8D (whitish-yellow).

*Pistils.*—Style and stigma: 5, very short, RHS 150D (pale-yellow). Ovary: 5-celled. Ovary length: 0.5 cm. Ovary color: RHS 143A (surface green).

Fruit and seed set: No seed set observed.

Disease and insect resistance: No particular resistance or susceptibility has been observed.

COMPARISON WITH PARENTAL AND COMMERCIAL CULTIVARS

'Fisnics Purdeep' differs from the female parent 'K02-1080-1' (unpatented) by having deep purple flowers and deep green foliage while 'K02-1080-1' has red-purple flowers and medium green foliage.

'Fisnics Purdeep' differs from the male parent 'K02-9604-2' (unpatented), by having deep purple flowers and narrower leaves, while 'K02-9604-2' has a deep cherry-red flower color.

'Fisnics Purdeep' differs from the commercial cultivar 'Fisimp 284' (U.S. Plant Pat. No. 13,694) by having larger flowers, and longer and somewhat deeper green leaves than 'Fisimp 284'.

'Fisnics Purdeep' differs from the commercial cultivar 'Fisnics Purpink' (U.S. Plant Patent applied for) by having a darker and more bluish flower color, with smaller flowers, and a more compact plant habit than 'Fisnics Purpink'.

'Fisnics Purdeep' differs from cultivar 'Fisupnic Purdeep' (U.S. Plant Patent applied for) by having larger flatter flowers, somewhat larger leaves and a more compact plant habit than 'Fisupnic Purdeep'.

I claim:

1. A new and distinct cultivar of New Guinea *Impatiens* plant as shown and described herein.

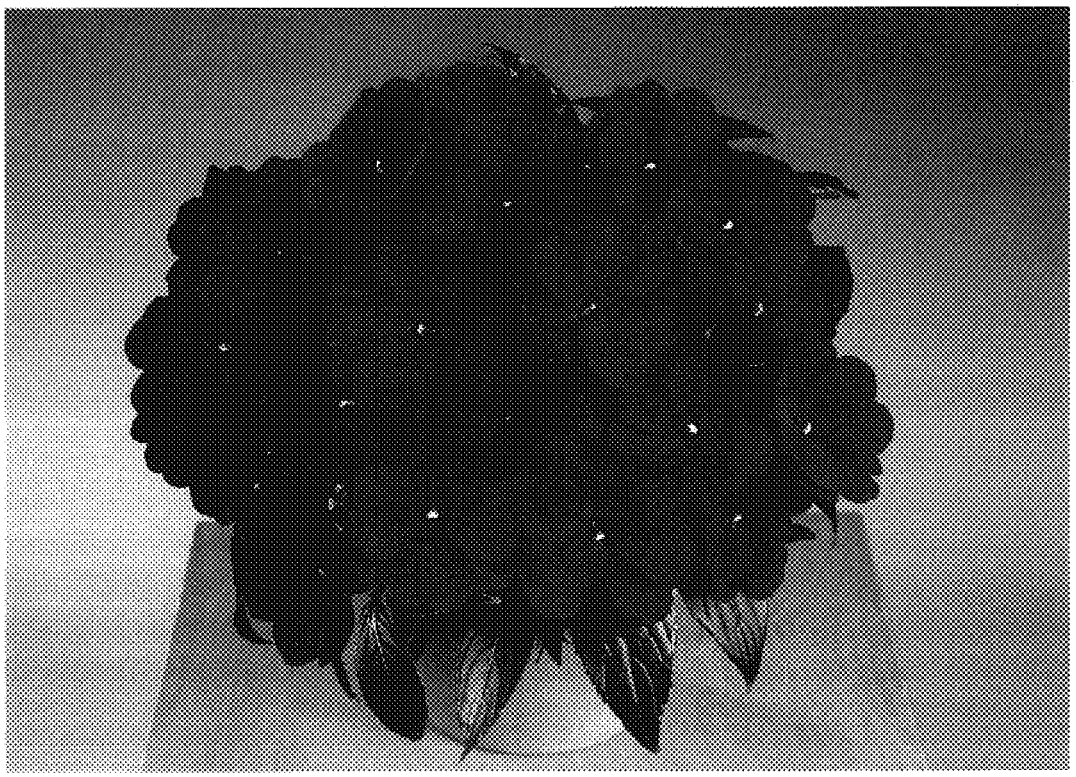

* * * * *